United States Patent
Natsch

(10) Patent No.: US 9,700,499 B2
(45) Date of Patent: Jul. 11, 2017

(54) ANTIMICROBIAL COMPOSITIONS

(75) Inventor: Andreas Natsch, Uetikon (CH)

(73) Assignee: GIVAUDAN SA, Vernier (CH)

( * ) Notice: Subject to any disclaimer, the term of this patent is extended or adjusted under 35 U.S.C. 154(b) by 571 days.

(21) Appl. No.: 12/097,958

(22) PCT Filed: Dec. 18, 2006

(86) PCT No.: PCT/CH2006/000707
§ 371 (c)(1),
(2), (4) Date: Jun. 18, 2008

(87) PCT Pub. No.: WO2007/071089
PCT Pub. Date: Jun. 28, 2007

(65) Prior Publication Data
US 2009/0004120 A1   Jan. 1, 2009

(30) Foreign Application Priority Data

Dec. 23, 2005  (GB) .................................. 0526283.7

(51) Int. Cl.
*A61K 8/33* (2006.01)
*A61K 8/34* (2006.01)
*A61Q 17/00* (2006.01)

(52) U.S. Cl.
CPC .................. *A61K 8/33* (2013.01); *A61K 8/34* (2013.01); *A61Q 17/005* (2013.01); *A61K 2800/524* (2013.01); *A61K 2800/59* (2013.01)

(58) Field of Classification Search
CPC .............................. A61K 31/045; A61K 47/10
See application file for complete search history.

(56) References Cited

U.S. PATENT DOCUMENTS

| | | | |
|---|---|---|---|
| 2,582,743 A * | 1/1952 | Bollmann et al. ............ | 560/231 |
| 5,670,160 A | 9/1997 | Eggensperger et al. | |
| 5,861,146 A | 1/1999 | Peterson et al. | |
| 6,878,381 B2 | 4/2005 | Collington | |
| 2002/0040139 A1* | 4/2002 | Billotte et al. ................ | 544/262 |
| 2007/0044174 A1* | 2/2007 | Havkin-Frenkel et al. .. | 800/278 |

FOREIGN PATENT DOCUMENTS

| | | | | |
|---|---|---|---|---|
| CA | 2270670 A1 * | 11/1999 | ............... | A61K 7/40 |
| EP | 0551975 A1 | 7/1993 | | |
| EP | 0570794 A | 11/1993 | | |
| EP | 1216691 A | 6/2002 | | |
| EP | 1238651 A1 | 9/2002 | | |
| GB | 2169807 * | 7/1986 | ............... | A01N 31/08 |
| JP | 6434909 * | 2/1989 | ............... | A61K 7/00 |
| JP | 2003192581 A | 7/2003 | | |
| WO | 03043621 A1 | 5/2003 | | |
| WO | 2004084855 A | 10/2004 | | |

OTHER PUBLICATIONS

English Language Abstract for EP0551975 taken from esp@cenet.com.
Allen L. Hall, "Phenoxyethanol—a Cosmetically Acceptable Preservative", Cosmetics & Toiletries, vol. 96, No. 3, pp. 83-85, Mar. 1981, XP 000617556.
Sequence listing XP-002426144, pp. 1-3, 2003.

* cited by examiner

*Primary Examiner* — Abigail Fisher
*Assistant Examiner* — Jessica Kassa
(74) *Attorney, Agent, or Firm* — Norris McLaughlin & Marcus PA

(57) ABSTRACT

Provided are personal care products and compositions that comprise at least one preservative compound selected from the group consisting of phenoxyethanol, 2-phenyl ethanol, phenoxypropanol, 3-phenylpropanol and benzylalcohol, in a total concentration of 0.1 to 1% (w/w); and at least one preservative enhancer compound selected from the group consisting of 4-methylbenzaldehyde, heliotropine, vanilline, 4-hydroxybenzaldehye, 3-hydroxybenzaldehyde, 4-methoxybenzaldehyde, 3-methoxybenzaldehyde, 2, 4-di-hydroxybenzaldehyde, 3-hydroxy-4-methoxybenzaldehyde, 3, 5-dihydroxybenzaldehyde, and 4-hydroxy-2-methoxybenzaldehyde, in a total concentration of 0.05 to 0.5% (w/w), in a cosmetically acceptable base. The composition does not contain certain classic bactericidal, fungicidal, sporicidal or preservative compounds. Further provided are methods of forming such compositions and products and the use of preservatives and preservative enhancers in such compositions and products.

24 Claims, No Drawings

ANTIMICROBIAL COMPOSITIONS

This is an application filed under 35 USC 371 of PCT/CH2006/000707.

Provided are preserved personal care product compositions and their use in personal care products applied to the human skin or scalp, and methods of making such products.

Preservatives are used in personal care products (products applied to the skin or scalp either to remain there or to be rinsed off to preserve these products against microbial spoilage and to extend their shelf life.

Antimicrobial compounds used for product preservation may fall into one or more of the following classes based on the effect they have on the microorganism, in particular bacteria and fungi. A germistatic compound inhibits the growth of germs, while a germicidal compound kills germs. An antibacterial or antifungal may inhibit growth of the microorganisms or kill them or both. Many antimicrobial compounds are not effective against fungal spores. A bacteriostatic compound inhibits growth of bacteria, while a bactericide kills bacteria (reduces their number). Similarly, a fungistatic compound inhibits the growth of fungi (molds and yeast), while a fungicide kills fungi (reduces their number). A sporicide kills spores of fungi or bacteria. Spores, especially endospores, are formed by some bacteria to survive during periods of deprivation and are significantly more difficult to kill. Fungi form spores for reproduction and these spores are significantly more difficult to kill than the vegetative form of the fungi.

A broad band preservative effect including a bactericidal and fungicidal activity was previously only partially attained in personal care products, or attained only by addition of certain fungicides, in particular formaldehyde, formaldehyde donors, halogenated compounds, compounds belonging to the class of parabens and a variety of specific fungicides.

Formaldehyde donors include in particular diazolidinyl urea (CAS 78491-02-8), imidazolidinyl urea (CAS 39236-46-9), and DMDM Hydantoin (CAS 6440-58-0).

Halogenated compounds include in particular 2,4-dichlorobenzyl-alcohol (CAS 1777-82-8), Chloroxylenol (also known as 4-chloro-3,5-dimethyl-phenol, CAS 88-04-0), Bronopol (also known as 2-bromo-2-nitropropane-1,3-diol, CAS 52-51-7), iodopropynyl butyl carbamate (CAS 55406-53-6).

Paraben compounds include in particular Methyl-paraben (CAS 99-76-3), Ethyl-paraben (CAS 120-47-8), Propyl-paraben (CAS 94-13-3), Butyl-paraben (CAS 94-26-8), Iso-propyl-paraben (CAS 4191-73-5), and Benzyl-paraben (CAS 94-18-8).

Other fungizides include Quaternium-15 (CAS 51229-78-8), methyl-chloroisothiazolinone (CAS 26172-55-4), and methylisothiazolinone (CAS 2682-20-4).

There are concerns that some of these fungicide compounds may constitute health hazards, for example, iodopropynyl butyl carbamate, formaldehyde and formaldehyde donors, methyl-chloroisothiazolinone (CAS 26172-55-4), and methylisothiazolinone are considered highly allergenic/sensitizing.

Accordingly there is an interest in replacing the above-mentioned compounds in personal care products applied to human skin or scalp while maintaining a good broad band preservative activity.

Various milder preservatives are known but do not provide a sufficient preservative effect. For example, phenoxyethanol, 2-phenylethanol, and benzyl alcohol are mild to the skin and do not raise similar safety concerns as do the preservatives mentioned above. However, these compounds on their own are able to provide a sufficient bactericidal activity only at a high concentration and even at a high concentration do not have a sufficient sporicidal effect.

JP2005053922 and JP2000143453 disclose hair cosmetics including shampoos that contain a large amount of phenoxyethanol. The comparatively large quantity of phenoxyethanol and its associated unpleasant smell is alleviated somewhat by the combination with benzaldehyde, which also has a very intensive smell which can be undesirable at higher concentrations in many personal care products.

Applicant has now identified compounds that, in combination with certain known preservatives (phenoxyethanol, 2-phenylethanol, benzyl alcohol), significantly enhance the preservative action in personal care products and provide a broad band preservative activity including a sporicidal effect. This is important for the stability and shelf life of the product.

The preservative enhancers are certain benzaldehyde-derivatives according to formula II as defined hereinbelow. The chemical structures of the preservative enhancers for use as defined herein are shown below.

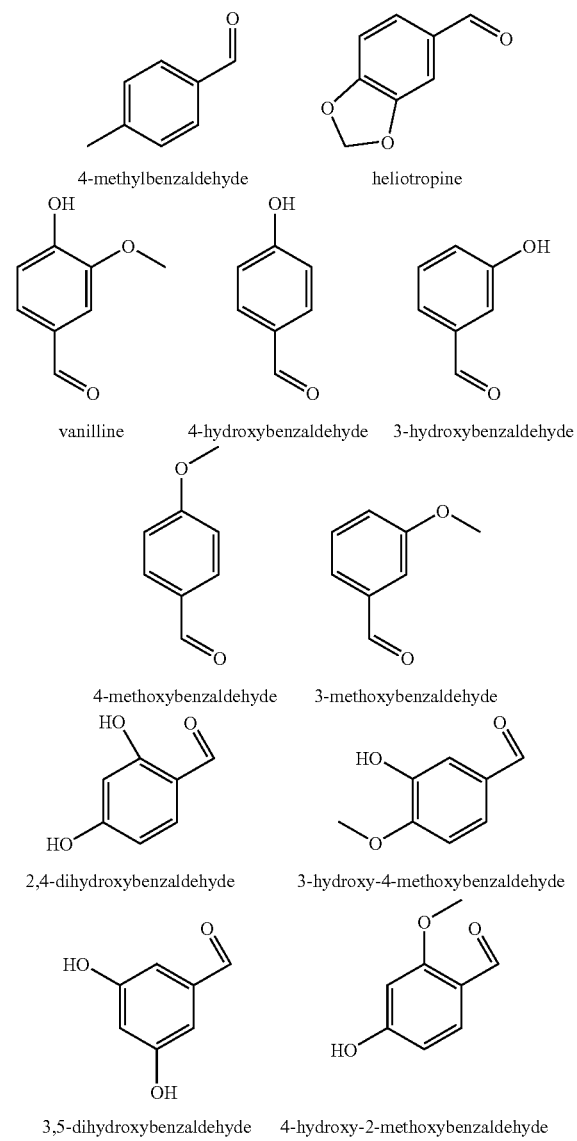

4-methylbenzaldehyde   heliotropine vanilline   4-hydroxybenzaldehyde   3-hydroxybenzaldehyde 4-methoxybenzaldehyde   3-methoxybenzaldehyde 2,4-dihydroxybenzaldehyde   3-hydroxy-4-methoxybenzaldehyde 3,5-dihydroxybenzaldehyde   4-hydroxy-2-methoxybenzaldehyde All preservative enhancer compounds for use as described herein are commercially available.

Some of these compounds have previously been shown to have a fungistatic effect against various food spoilage molds and yeasts. The antifungal activity of a given antifungal against a given fungal species varies with the food product in which it is used, possibly due to the concentration of lipids or proteins. Fitzgerald et al. report vanillin and various derivatives to have antifungal (fungistatic) activity against a variety of food molds including various *Aspergillus* species (*A. oryzae, A sojae*), *Penicillium* species, and yeast strains when tested in yeast extract peptone dextrose broth. The efficacy against various fungal strains varies. Fungicidal or sporicidal activities were not tested. (J. Agric. Food Chem. 2005, 53, 1769-1775).

Similarly, heliotropin is known to be active as a fungistatic compound in vaporous form when applied to fungi on tobacco leaves, and to have an antifungal and antibacterial effect against some fungi and bacteria in aqueous culture media.

While many substituted benzaldehydes and benzylalcohols are known to have a germistatic activity against some microorganisms, the germicidal effect, in particular the bactericidal and fungicidal effect, is generally considered to be low, especially when the pH is within the range commonly used in personal care products which is pH 5 to pH 9. While some compounds are known to be more active under extremely acidic or alkaline conditions, this effect does not extend to the pH range used in personal care products.

That compounds that are fungistatic in certain food stuffs can provide a fungicidal and sporicidal effect in personal care products that often contain lipids and proteins or a high concentration of detergents was completely surprising and could not have been predicted. As can be seen from the examples in this application, an activity or lack of activity of a given test compound in water is not indicative of an activity in a personal care product, for example a cosmetic cream. In particular, an enhancing effect when used in combination with certain known preservatives in personal care products is not predictable.

The chemical structures of the preservative compounds useful in compositions and personal care products as defined herein are shown below. These are commonly used in personal care products.

A compound of formula I

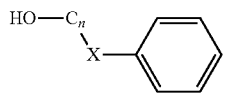

I wherein X is selected from C and O, and n is selected from 0, 1, 2, and 3,
wherein if X is O, then n is selected from 2 and 3, and when X is C, then n is selected from 0, 1, and 2.

Formula I therefore encompasses compounds selected from the group consisting of phenoxyethanol, 2-phenylethanol, benzylalcohol, 3-phenoxypropanol, and 3-phenylpropanol, whose structures are shown herein below.

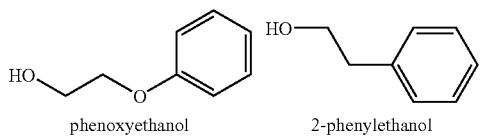

phenoxyethanol     2-phenylethanol

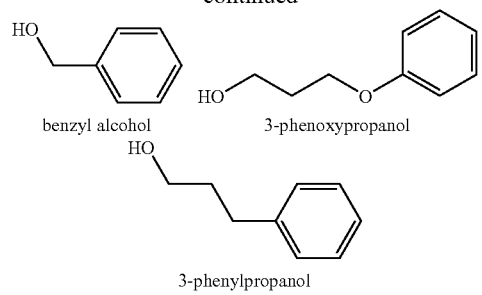

benzyl alcohol     3-phenoxypropanol 3-phenylpropanol

Of interest are also compounds of formula I as shown herein-above wherein X is selected from C and O, and n is selected from 0, 1 and 2, and
wherein if X is O, then n is 2, if X is C, then n is selected from 0 and 1.

Formula I therefore encompasses compounds selected from the group consisting of phenoxyethanol, 2-phenylethanol, and benzylalcohol, whose structures are shown herein above.

SUMMARY

In a first aspect, there is provided a personal care product composition comprising
a) at least one compound of formula I

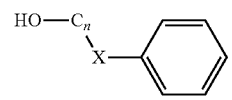

I wherein X is selected from C and O, and n is selected from 0, 1, 2, and 3,
wherein if X is O, then n is selected from 2 and 3, and when X is C, then n is selected from 0, 1, and 2,
wherein said compound is selected from the group consisting of phenoxyethanol, 2-phenylethanol, benzylalcohol, 3-phenoxypropanol, and 3-phenylpropanol, and
wherein the at least one compound of formula I is present in a total concentration of 0.1 to 1% (w/w);
b) at least one benzaldehyde-derivative compound according to formula II

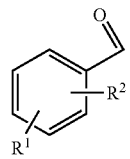

II wherein R1 and R2 are selected from H, methyl, hydroxy, methoxy, or R1 together with R2 forms a 3,4-methylendioxy substituent, and
wherein if R1 is H then R2 is selected from methyl, hydroxy, and methoxy, and
wherein if R2 is hydroxy, then R1 is selected from H, hydroxy, and methoxy, and
wherein said benzaldehyde-derivative compound is selected from the group consisting of 4-methylbenzaldehyde, heliotropine, vanilline, 4-hydroxybenzaldehye, 3-hydroxybenzaldehyde, 4-methoxybenzaldehyde, 3-methoxybenzaldehyde, 2,4-dihydroxybenzaldehyde, 3-hydroxy-4-methoxybenzaldehyde, 3,5-dihydroxybenzaldehyde, and 4-hydroxy-2-methoxybenzaldehyde; and wherein the at least one benzaldehyde-derivative compound according to formula II is present in a total concentration from 0.05 to 0.5% (w/w);

and a cosmetically-acceptable base, with the proviso that the composition is free from a bactericidally-, fungicidally-, sporicidally-effective or preservative concentration of compounds selected from the group consisting of:

formaldehyde; a formaldehyde donor compound including but not limited to diazolidinyl urea, imidazolidinyl urea, and DMDM Hydantoin;

a halogenated compound including but not limited to 2,4-dichlorobenzyl-alcohol, 4-chloro-3,5-dimethyl-phenol, 2-bromo-2-nitropropane-1,3-diol, and iodopropynyl butyl carbamate;

a parabene compound, including methyl-parabene, ethyl-parabene, propyl-parabene, butyl-parabene, isopropyl-parabene, and benzyl-parabene;

and a fungicide selected from quaternium-15 (CAS 51229-78-8), methyl-chloroisothiazolinone, and methylisothiazolinone.

Further there is provided a personal care product composition as hereinabove described wherein the at least one compound a) is present in a concentration selected from 0.2 to 0.9%, 0.2 to 0.8%, and 0.3 to 0.6% (w/w);

a personal care product composition as described above wherein the at least one compound b) is present in a concentration selected from 0.075 to 0.3%, and 0.1 to 0.2% (w/w);

a personal care product composition as hereinabove described wherein the at least one compound a) is present in a concentration of 0.2 to 0.8% (w/w), and wherein the at least one compound b) is present in a concentration selected from 0.075 to 0.3%, and 0.1 to 0.2% (w/w);

and a personal care product composition as hereinabove described wherein the at least one compound a) is present in a concentration of 0.3 to 0.6% (w/w), and wherein the at least one compound b) is present in a concentration selected from 0.075 to 0.3%, and 0.1 to 0.2% (w/w).

Still further there is provided a personal care product composition as hereinabove described selected from compositions for personal care products applied to and left on the skin or scalp including creams, salves, lotions, and ointments for hand, face or body, perfumes, eau de Cologne, eau de toilet, deodorants, antiperspirants, and products applied to and rinsed off the skin or scalp including soaps, liquid soaps, shower gels, and shampoos.

In another aspect there is provided a personal care product comprising a personal care product composition as hereinabove described, in an application form selected from stick, roll-ons, spray, pump-spray, aerosol, soap bar, powder, solution, gel, cream, balm and lotion.

In still another aspect there is provided a personal care product or composition therefor as hereinabove described wherein the personal care product composition comprises lipids.

In a particular embodiment, the above lipid-comprising personal care product composition is provided in form of an emulsion.

In yet another aspect, there is provided a personal care product or composition therefor as hereinabove described wherein the pH is 5 to 9.

In a further aspect there is provided the use of at least one compound a) as hereinabove defined and at least one compound b) as hereinabove defined, for the preparation of a preserved personal care product composition, or a preserved personal care product.

In another aspect there is provided a method of forming a preserved personal care product composition which is sufficiently bactericidal to have a reduction factor for *Pseudomonas aeruginosa* and *Staphylococcus aureus* of at least 1000 per 7 days, and is sufficiently sporicidal to have a reduction factor of 100 per 7 days for *Aspergillus niger*, by admixing an effective amount of the at least one compound a) and the at least one compound b) as hereinabove defined to a personal care product base, forming a personal care product composition with the proviso as hereinabove defined.

In another aspect there is provided a method of making a preserved personal care product by providing the personal care product composition formed as hereinabove described in a suitable personal care product application form that includes sticks, roll-ons, sprays, pump-sprays, aerosols, soap bars, powders, solutions, gels, creams, balms and lotions.

Bases for personal care products are well known in the art and the resulting personal care product will usually have a pH of pH5 to pH9 (for example, slightly acidic for products applied to and left on the skin, slightly alkaline for soap products). It is also possible to employ an existing personal care product composition and simply add a) and b) in the concentrations hereinabove defined and mix thoroughly.

The exact concentration of compounds under a) and b) that is employed in a composition will depend upon the nature of the product and the preservative effect and length to be achieved, in particular the bactericidal, fungicidal and sporicidal activity.

A useful concentration for the preservative compound a) is, for example, 0.1 to 1%, 0.2 to 0.8% or 0.3 to 0.6% (w/w).

A useful concentration for the preservative enhancer compound b) is, for example, 0.05 to 5%, 0.075 to 0.3%, or 0.1 to 0.2% (w/w).

In the given concentrations, the preservative a) and the preservative enhancer b) generally provide a sufficient bactericidal, fungicidal and sporicidal activity in a wide range of personal care product compositions.

In particular, a sufficient bactericidal activity is attained when the reduction factor is 1000 per 7 days. A sufficient sporicidal activity is attained when the reduction factor is 100 per 7 days. A sufficient sporicidal activity is strongly indicative of a sufficient fungicidal activity. Fungicidal activity may easily be tested on yeast strains, using a mix of three *Candida* strains as described in example 4. A sufficient fungicidal activity is reached when the reduction factor is 100 per 7 days.

The reduction factor is determined by growing a suitable test organism (*Aspergillus niger* for fungi, *Pseudomonas aeruginosa* for gram-negative bacteria and *Staphylococcus aureus* for gram-positive bacteria) on a suitable culture medium on agar plates, harvesting and adding to a personal care product composition in a density of $3 \times 10^5$ organism/ml and counting the plated organisms in the probe and a negative control. The count of the negative control is divided by the count of the probe and thereby the reduction factor is determined (compare example 1).

Preservative enhancers of particular interest are 4-hydroxybenzaldehyde and 3-hydroxybenzaldehyde, for their surprisingly good activity.

The addition of hydroxy groups to benzaldehyde and derivatives was previously shown not to provide a fungicidal effect on *A. niger*.

Fitzgerald et al (who looked at fungistatic effects only, and only of certain food-relevant fungi excluding *A. niger*), found that the removal of hydroxy groups from 4-hydroxybenzaldehyde resulted in a slight improvement of fungistatic activity against certain food molds, and the only position beneficial for antifungal (fungistatic) activity was the 2-OH position within the benzene ring of benzaldehyde (J. Agric. Food Chem. 2005, 53, 1769-1775).

Furthermore the abovementioned compounds have only a low fragrance intensity. While highly fragrant compounds such as vanillin are restricted in their usefulness in personal care products depending on the fragrance note to be achieved (which may not be compatible), the abovementioned compounds can be combined with almost any personal care product without significantly altering the fragrance profile.

Personal care product compositions are used to form a personal care product in an appropriate application form and packaging, as is well-known in the art.

Personal care products and compositions to form them as described herein are used for the purpose of cleansing, conditioning, grooming, beautifying, promoting attractiveness, or otherwise enhancing or altering the appearance of the human body and are applied to the human skin or scalp.

These include products applied to and left on the skin or scalp, for example creams, salves, lotions, and ointments for hand, face or body, perfumes, eau de Cologne, eau de toilet, deodorants, antiperspirants, and products applied but rinsed off such as soaps, liquid soaps, shower gels, shampoos.

These products can, for example, take various forms of application, for example sticks, roll-ons, sprays, pump-sprays, aerosols, soap bars, powders, solutions, gels, creams, balms and lotions.

Many personal care products will be formulated as an emulsion or other lipid-containing products and these form a particular aspect of the embodiments described-herein. Lipids are often included for example into washing formulations including liquid soaps or washing lotions to provide an oil replenishing effect. Preservative-enhancing compounds as hereinabove defined allow the formulation of preserved emulsions or formulations comprising lipids and/or detergents where the activity (the bactericidal, fungicidal and in particular the sporicidal effect) is not lost due to the presence of the lipid base and/or detergents or surfactants.

Depending on the nature of the personal care product, personal care product compositions as described herein may also be combined with art-recognised quantities of other excipients commonly employed in these products; useful selections may be found in <<CTFA Cosmetic Ingredient Handbook>>, J. M. Nikitakis (ed.), 1st ed., The Cosmetic, Toiletry and Fragrance Association, Inc., Washington, 1988, which is hereby incorporated by reference.

In general, excipients may, for example, include colorants, fragrances, solvents, surfactants, colorants, opacifiers, buffers, antioxidants, vitamins, emulsifiers, UV absorbers, silicones and the like. All products can also be buffered to the desired pH using commonly-available excipients in a known manner.

There now follows a series of non-limiting examples that serve to illustrate the invention.

While the personal care product compositions, products, and related methods have been described above in connection with certain illustrative embodiments, it is to be understood that other similar embodiments may be used or modifications and additions may be made to the described embodiments for performing the same function. Further, all embodiments disclosed are not necessarily in the alternative, as various embodiments may be combined to provide the desired characteristics. Variations can be made by one having ordinary skill in the art without departing from the spirit and scope of the disclosure. Therefore, the compositions, products and methods should not be limited to any single embodiment, but rather construed in breadth and scope in accordance with the recitation of the attached claims.

EXAMPLE 1

Sporicidal Effect of Test Compounds in Water

*Aspergillus niger* ATCC 16404 spores are added to water to obtain a density of $3 \times 10^5$ spores/ml. In order to prepare the spores, the test strain is grown for 5 days on potato dextrose agar at room temperature. The spores are harvested with a solution containing 0.1% Tween 80, peptone 0.1% and NaCl 0.85% and the spore concentration is adjusted to the density indicated above.

Test compounds are dissolved in dipropyleneglycol to a concentration of 20%.

These stock solutions are added to 10 ml aliquots of the spore suspension to obtain a final concentration of the test compounds of 0.1%. The sporicidal effect is shown by a reduction of spore counts after 7 days.

The reduction factor is determined as follows. Aliquots of the above prepared suspension of microorganisms (here: spore suspension prepared as described above) are plated on a suitable agar medium (see above) and the developing colonies are counted both for samples with test compound and for a negative probe (water). The count of the negative control is divided by the count of the test compound and thereby the reduction factor is determined. A negative control (water) accordingly has a reduction factor of 1 (no effect on the microorganism).

TABLE 1

Sporicidal effect of test compounds in water

| | 0.1% test compound | |
|---|---|---|
| Test compound | Spores/ml | Reduction factor |
| Negative control (water) | $2.5 \times 10^5$ | 1 |
| Cuminic alcohol | $>1.2 \times 10^5$ | <2 |
| Mefranal (3-methyl-5-phenylpentanal) | $4 \times 10^3$ | 63 |
| 9-decen-1-ol | $1.1 \times 10^4$ | 23 |
| 4-hydroxybenzaldehyde | $>1.2 \times 10^5$ | <2 |
| 4-methoxy-benzaldehyde | $4.68 \times 10^4$ | 5 | n.d. not determined

No significant reduction of spore counts is achieved with 4-hydroxybenzaldehyde and 4-methoxybenzaldehyde.

Mefranal, and and 9-decenol show a significant sporicidal effect.

EXAMPLE 2

Sporicidal Effect of Test Compounds and Preservatives in a Cosmetic Cream

A cosmetic cream (pH 5.5) for application to the human skin is formulated as follows (in % w/w):

| | |
|---|---|
| Glyceryl-monostearate | 3 |
| Glycerine | 5 |
| Xanthan gum | 0.25 |
| Stearic acid | 7 |
| Sweet almond oil | 4 |
| Glyceryl dilaurate | 1 |
| Cetyl-stearyl-alcohol | 2 |
| L-Arginine | 0.5 |
| Water | add 100 |

Glyceryl-monostearate, Sweet almond oil, Cetyl-stearyl-alcohol and Glyceryl dilaurate are melted at 80° C. Xanthan gum is dispersed into glycerine. Arginine is dissolved in water and heated to 75° C. The Xanthan gum-glycerin suspension is added to the heated water phase, the heated oil phase is added and the suspension is stirred at 300 rpm for 10 min whilst being cooled down slowly. Finally, a homogeneous emulsion is made with a high speed homogenizer at 5000 rpm.

Test samples of cream contain different amounts of preservatives and/or preservative enhancer. The preservative and preservative enhancer is added to an aliquot of 10 g of the cream in 50 ml tubes to a concentration (w/w) of 0.1-0.5% as shown in the table below. After addition of the preservative/preservative enhancer, the cream is thoroughly mixed to achieve a homogeneous distribution.

After 1-3 days of equilibration of the cream (storage at room temperature to achieve a homogenous partitioning of compounds between oil and water phase), to each sample 100 µl of a spore suspension of *Aspergillus niger* ATCC 16404 containing $3 \times 10^7$ spores/ml (prepared as described in example 1) is added. After regular test intervals, samples of 1 g cream are removed and added to 20 ml of a neutralizer solution containing 0.2% lecithin, 2% Tween 80 and 0.5% NaCl. These dilutions are vigorously shaken for 10 min until the cream is dissolved, and then aliquots of this solution are spread plated on potato dextrose agar containing 0.2% Tween 80. After 48 h to 72 h the number of surviving colony forming units (and therefore surviving spores) are counted.

Table 2 shows the effects of test compounds combined with phenoxyethanol

TABLE 2

Sporicidal effect of cream samples with test compounds and phenoxyethanol

| Test agent | Spores/ml after 7 d | Reduction factor |
|---|---|---|
| Comparative Control (0.5% Phenoxyethanol only) | $7.37 \times 10^4$ | |
| | 0.2% test compound and 0.5% phenoxyethanol | |
| Mefranal (3-methyl-5-phenylpentanal) | $3.12 \times 10^4$ | 1.6 |
| 9-decenol | $2.44 \times 10^4$ | 2.1 |
| 4-methoxybenzaldehyde | <100 | >737 |
| | 0.1% test compound and 0.5% phenoxyethanol | |
| Benzaldehyde | <100 | >737 |
| 4-methylbenzaldehyde | <100 | >737 |
| Heliotropine | <100 | >737 |
| Vanilline | <100 | >737 |
| 4-hydroxybenzaldehyde | <100 | >737 |
| 3-hydroxybenzaldehyde | <100 | >737 |
| 4-methoxybenzaldehyde | <100 | >737 |
| 3-methoxybenzaldehyde | <100 | >737 |

Not all compounds of similar structure show the enhancing effect: Mefranal and 9-decenol (the compounds which have a sporicidal effect when used on their own in water at 0.1%), do not show an enhancing effect in the cosmetic cream in presence of phenoxyethanol, even at 0.2% concentration of Mefranal or 9-decenol.

Surprisingly, though 4-hydroxybenzaldehyde and 4-methoxy-benzaldehyde show no significant sporicidal effect in water, these and several other test compounds show an excellent enhancing activity in cream at 0.1% concentration (complete killing of spores within 7 days).

EXAMPLE 3

Enhanced Sporicidal Effect of Preservative Compounds in Cosmetic Cream

The sporidical effect in cream (prepared as described in example 2) is compared when using the test compounds alone or in combination with phenoxyethanol, benzyl alcohol or 2-Phenylethanol.

Table 3 shows the sporicidal effect of test compounds in the presence of various preservatives (phenoxyethanol, benzyl alcohol or 2-Phenylethanol).

TABLE 3

Sporicidal effect of test compounds and various preservatives

| Test compound | Preservative | Spores/ml after 7 d | Reduction factor |
|---|---|---|---|
| none | none | $1.04 \times 10^5$ | |
| none | Phenoxyethanol 0.5% | $6.8 \times 10^4$ | 1.5 |
| none | 2-Phenylethanol 0.5% | $4.2 \times 10^4$ | 2.5 |
| none | 2-Phenylethanol 0.25% + benzylalcohol 0.25% | $2.12 \times 10^4$ | 4.9 |
| none | 2-Phenylethanol 0.5% + benzylalcohol 0.5% | $4.8 \times 10^3$ | 21.7 |
| 4-methoxybenzaldehyde 0.1% | none | $2.8 \times 10^3$ | 37.1 |
| Vanilline 0.1% | none | $1 \times 10^4$ | 10.4 |
| 4-hydroxybenzaldehyde 0.1% | none | $1.0 \times 10^5$ | 1.04 |
| 4-hydroxy-2-methoxy-benzaldehyde | none | $2.08 \times 10^4$ | 5 |
| 3,5-dihydroxybenzaldehyde | none | $1 \times 10^4$ | 10 |
| 4-methoxybenzaldehyde 0.1% | Phenoxyethanol 0.5% | <100 | >1040 |
| Vanilline 0.1% | Phenoxyethanol 0.5% | <100 | >1040 |
| 4-hydroxybenzaldehyde 0.1% | Phenoxyethanol 0.5% | <100 | >1040 |
| 4-hydroxy-2-methoxy-benzaldehyde | Phenoxyethanol 0.5% | <100 | >1040 |
| 3,5-dihydroxybenzaldehyde | Phenoxyethanol 0.5% | <100 | >1040 |

TABLE 3-continued

Sporicidal effect of test compounds and various preservatives

| Test compound | Preservative | Spores/ml after 7 d | Reduction factor |
|---|---|---|---|
| 4-hydroxybenzaldehyde 0.1% | 2-Phenylethanol 0.5% | <100 | >1040 |
| 4-hydroxybenzaldehyde 0.1% | 2-Phenylethanol 0.25% + benzylalcohol 0.25% | <100 | >1040 |
| 4-hydroxybenzaldehyde 0.1% | 2-Phenylethanol 0.5% + benzylalcohol 0.5% | <100 | >1040 |

The results in table 3 show that the sporicidal effect on *Aspergillus niger* spores is only achieved when combining test compounds with either phenoxyethanol, 2-phenylethanol or 2-phenylethanol/benzyl alcohol. Neither the test compounds alone nor the preservatives alone achieve the sporicidal effect necessary for preservation of personal care products.

EXAMPLE 4

Broad Band Activity Against Bacteria, Yeast and Mold Spores in Cosmetic Cream

As test organisms *Staphylococcus aureus* (DSMZ 799) and *Pseudomonas aeruginosa* (ATCC 15442) are used. The strains are grown overnight in Mueller-Hinton broth and adjusted to a cell density of $1 \times 10^8$ cfu (colony forming units) per ml.

The two bacterial strains are mixed in a ratio of 1:1 and 100 μl of this mixed inoculum is added to 10 ml aliquots of the cosmetic cream supplemented with test compounds as described in Example 2 in the concentration as indicated in the table below.

The resulting mixtures are incubated at room temperature and at the regular intervals samples are removed, suspended in neutralizer solution and diluted as described above (example 2).

Aliquots of these suspended and diluted samples are plated on tryptic soy agar supplemented with 0.5% Tween 80 and then incubated for 24 h at 37° C. Surviving bacteria are counted.

The same procedure as described above except for the changes mentioned below is performed with a mixture of the three yeast strains *Candida albicans* ATCC 10231, *Candida guilliermondii* ATCC 6260 and *Candida parapsilosis* ATCC 22019 that replace the bacterial strains.

The yeast strains are grown in Sabouraud liquid medium, washed and suspended in saline and adjusted to $5 \times 10^7$ cfu (colony forming units) per ml. The Inoculum of the three strains is then pooled in a ratio of 1:1:1. For determining the reduction factor by counting of the colonies formed, the samples inoculated with the yeast strains are spread plated on potato dextrose, incubated until colonies have formed and counted.

Table 4 shows the results.

TABLE 4

Activity of test compositions against bacteria and yeasts

| | | Bacteria (cfu/g cream) | | Yeasts (cfu/g cream) | |
|---|---|---|---|---|---|
| Test compound 0.1% | Preservative 0.5% | 24 h | 7 d | 48 h | 7 d |
| none | None | $3 \times 10^5$ | $3 \times 10^5$ | $2.7 \times 10^5$ | $2.2 \times 10^5$ |
| none | Phenoxyethanol | $2.42 \times 10^5$ | $4.1 \times 10^4$ | $1.94 \times 10^5$ | $1.1 \times 10^4$ |
| 4-hydroxybenzaldehyde | none | $3.8 \times 10^3$ | $1.28 \times 10^4$ | $7.4 \times 10^3$ | $2.2 \times 10^5$ |
| 4-hydroxybenzaldehyde | Phenoxyethanol | $1.9 \times 10^4$ | <200 | <200 | <200 |
| 4-hydroxybenzaldehyde | 2-Phenylethanol | $1 \times 10^3$ | <200 | <200 | <200 |

EXAMPLE 5

Enhancing Effect of Test Compounds on Preservatives

The experiments described in example 2-4 are performed with varying concentrations of test compound and preservative as indicated in Table 5. The table indicates the concentrations in which test compound and preservative are tested in weight percent, and the results show the reduction factors (calculated as described herein-above) for a mix of bacteria (prepared as described in example 4) and *A. niger* after 24 hours or 7 days.

The results show an enhancing effect of the test compound (4-hydroxybenzaldehyde) in presence of the preservative compound (phenoxyethanol).

TABLE 5

Enhancing effect of test compounds on preservatives

| test compound (% w/w) | preservative (% w/w) | Reduction factor *A. niger*, 7 d |
|---|---|---|
| 0 | 0 | 1 |
| 0 | 1 | 236 |
| 0 | 0.8 | 16 |
| 0.05 | 0.5 | 66 |
| 0.1 | 0.5 | >1180 |
| 0.1 | 0.3 | 295 |
| 0.1 | 0 | 2 |

The invention claimed is:

1. A method for enhancing the bactericidal preservative activity of a preservative compound in a personal care product composition, the method comprising the steps of:
   providing at least one preservative compound a) selected from the group consisting of phenoxyethanol, 2-phenylethanol, 3-phenoxypropanol, and 3-phenylpropanol, wherein the at least one preservative compound a) is present in a total concentration of 0.2 to 1% (w/w);

providing at least-one preservative enhancing benzaldehyde-derivative compound b) selected from the group consisting of: 4-methylbenzaldehyde, heliotropine, 4-hydroxybenzaldehyde, 3-hydroxybenzaldehyde, 4-methoxybenzaldehyde, 3-methoxybenzaldehyde, 3,5-dihydroxybenzaldehyde, and 4-hydroxy-2-methoxybenzaldehyde, wherein the at least one preservative enhancing compound b) is present in a total concentration of 0.075 to 0.5% (w/w); and, enhancing preservative activity in a personal care product composition by admixing an effective amount of the at least one preservative compound a) and the at least one preservative enhancer compound b) with a personal care product base to form the personal care product composition which has a reduction factor for *Pseudomonas aeruginosa* and *Staphylococcus aureus* of at least 1000 per 7 days;

with the proviso that: the personal care product composition is free from a bactericidally-, fungicidally-, sporicidally-effective or preservative concentration of compounds selected from the group consisting of: formaldehyde; a formaldehyde donor compound selected from including diazolidinyl urea, imidazolidinyl urea, and DMDM Hydantoin; a halogenated compound selected from including 2,4-dichlorobenzyl-alcohol, 4-chloro-3,5-dimethyl-phenol, 2-bromo-2-nitropropane-1,3-diol, and iodopropynyl butyl carbamate; a parabene compound selected from, including methyl-parabene, ethyl-parabene, propyl-parabene, butyl-parabene, isopropyl-parabene, and benzyl-parabene; and a fungicide selected from quaternium-15 (CAS 51229-78-8), methyl-chloroisothiazolinone, and methylisothiazolinone.

2. The method according to claim 1, wherein the at least one preservative compound a) is present in a total concentration of 0.2% to 0.8% (w/w).

3. The method according to claim 1, wherein the at least one preservative compound a) is present in a total concentration of 0.2% to 0.6% (w/w).

4. The method according to claim 1, wherein the at least one preservative compound a) is present in a total concentration of 0.3% to 0.6% (w/w).

5. The method according to claim 1, wherein the at least-one preservative enhancing benzaldehyde-derivative compound b) is present in a total concentration of 0.1% to 0.5% (w/w).

6. The method according to claim 1, wherein the at least-one preservative enhancing benzaldehyde-derivative compound b) is present in a total concentration of 0.075% to 0.3% (w/w).

7. The method according to claim 1, wherein the at least-one preservative enhancing benzaldehyde-derivative compound b) is present in a total concentration of 0.075% to 0.2% (w/w).

8. The method according to claim 1, wherein the personal care product composition is selected from the group consisting of: stick, roll-on, spray, pump-spray, aerosol, soap bar, powder, solution, gel, cream, balm, lotion, salve, and topical ointment.

9. The method according to claim 8, wherein the personal care product compositions are selected from perfumes, eau de Cologne, eau de toilet, deodorants, antiperspirants, soaps, liquid soaps, shower gels, and shampoos.

10. The method according to claim 1, wherein the personal care product composition is selected from the group consisting of: (1) a personal care product composition which is applied to and left on the skin or scalp and, (2) a personal care product compositions which is rinsed off after being applied.

11. The method according to claim 1, wherein the personal care product composition contains lipids or is an emulsion.

12. The method according to claim 1, wherein the personal care product composition has a pH of from 5 to 9.

13. A method for enhancing the fungicidal preservative activity of a preservative compound in a personal care product composition, the method comprising:

providing at least one preservative compound a) selected from the group consisting of phenoxyethanol, 2-phenylethanol, 3-phenoxypropanol, and 3-phenylpropanol, wherein the at least one preservative compound a) is present in a total concentration of 0.3 to 1% (w/w);

providing at least-one preservative enhancing benzaldehyde-derivative compound b) selected from the group consisting of: 4-methylbenzaldehyde, heliotropine, 4-hydroxybenzaldehyde, 3-hydroxybenzaldehyde, 4-methoxybenzaldehyde, 3-methoxybenzaldehyde, 3,5-dihydroxybenzaldehyde, and 4-hydroxy-2-methoxybenzaldehyde, wherein the at least one preservative enhancing compound b) is present in a total concentration of 0.1 to 0.5% (w/w); and, enhancing preservative activity in a personal care product composition by admixing an effective amount of the at least one preservative compound a) and the at least one preservative enhancer compound b) with a personal care product base to form the personal care product composition which has a reduction factor for *Aspergillus niger* of at least 100 per 7 days;

with the proviso that: the composition is free from a bactericidally-, fungicidally-, sporicidally-effective or preservative concentration of compounds selected from the group consisting of: formaldehyde; a formaldehyde donor compound selected from including diazolidinyl urea, imidazolidinyl urea, and DMDM Hydantoin; a halogenated compound selected from including 2,4-dichlorobenzyl-alcohol, 4-chloro-3,5-dimethyl-phenol, 2-bromo-2-nitropropane-1,3-diol, and iodopropynyl butyl carbamate; a parabene compound selected from, including methyl-parabene, ethyl-parabene, propyl-parabene, butyl-parabene, isopropyl-parabene, and benzyl-parabene; and a fungicide selected from quaternium-15 (CAS 51229-78-8), methyl-chloroisothiazolinone, and methylisothiazolinone.

14. The method according to claim 13, wherein the at least one preservative compound a) is present in a total concentration of 0.2% to 0.8% (w/w).

15. The method according to claim 13, wherein the at least one preservative compound a) is present in a total concentration of 0.3% to 0.6% (w/w).

16. The method according to claim 13, wherein the at least-one preservative enhancing benzaldehyde-derivative compound b) is present in a total concentration of 0.1% to 0.3% (w/w).

17. The method according to claim 13, wherein the at least-one preservative enhancing benzaldehyde-derivative compound b) is present in a total concentration of 0.1% to 0.2% (w/w).

18. The method according to claim 13, wherein the personal care product composition is selected from the group consisting of: stick, roll-on, spray, pump-spray, aerosol, soap bar, powder, solution, gel, cream, balm, lotion, salve, and topical ointment.

19. The method according to claim 18, wherein the personal care product compositions are selected from perfumes, eau de Cologne, eau de toilet, deodorants, antiperspirants, soaps, liquid soaps, shower gels, and shampoos.

20. The method according to claim 13, wherein the personal care product composition is a selected from the group consisting of: (1) a personal care product composition which is applied to and left on the skin or scalp and (2) a personal care product composition which is rinsed off after being applied.

21. The method according to claim 13, wherein the personal care product composition contains lipids or is an emulsion.

22. The method according to claim 13, wherein the personal care product composition has a pH of from 5 to 9.

23. The method according to claim 13, wherein the formed personal care product composition has a reduction factor for *Aspergillus niger* in excess of 737 in 48 hours.

24. The method according to claim 13, wherein the formed personal care product composition has a reduction factor for *Aspergillus niger* in excess of 1040 in 48 hours.

* * * * *